United States Patent
Joosten et al.

(10) Patent No.: US 7,660,381 B2
(45) Date of Patent: Feb. 9, 2010

(54) SCATTER COMPENSATION IN AN X-RAY SYSTEM

(75) Inventors: Johannes Henricus Maria Joosten, Eindhoven (NL); Miels Noordhoek, Eindhoven (NL); Herman Stegehuis, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 267 days.

(21) Appl. No.: 11/719,555

(22) PCT Filed: Nov. 17, 2005

(86) PCT No.: PCT/IB2005/053802

§ 371 (c)(1), (2), (4) Date: May 17, 2007

(87) PCT Pub. No.: WO2006/056915

PCT Pub. Date: Jun. 1, 2006

(65) Prior Publication Data

US 2009/0147911 A1    Jun. 11, 2009

(30) Foreign Application Priority Data

Nov. 23, 2004   (EP)   ................................. 04105997

(51) Int. Cl.
*A61B 6/00*   (2006.01)

(52) U.S. Cl. ............................. 378/7; 378/207; 378/901
(58) Field of Classification Search .................... 378/4, 378/5, 7, 19, 98.8, 98.11, 98.12, 145, 147, 378/149, 207, 901
See application file for complete search history.

(56) References Cited

U.S. PATENT DOCUMENTS

| 4,549,307 | A |   | 10/1985 | Macovski ................... 378/145 |
| 4,741,009 | A |   | 4/1988 | Yamagata et al. .......... 378/98.4 |
| 4,995,107 | A | * | 2/1991 | Klingenbeck .................. 378/7 |
| 5,533,088 | A |   | 7/1996 | Fivez ........................ 378/98.4 |
| 6,134,297 | A |   | 10/2000 | Chao ....................... 378/98.12 |
| 6,633,626 | B2 |   | 10/2003 | Trotter et al. ................. 378/62 |
| 2002/0048339 | A1 |   | 4/2002 | Schneider et al. ............... 378/7 |
| 2003/0198314 | A1 |   | 10/2003 | Saito .............................. 378/4 |
| 2004/0120457 | A1 |   | 6/2004 | Karellas et al. ............... 378/62 |

* cited by examiner

*Primary Examiner*—Courtney Thomas

(57) ABSTRACT

Scatter compensation is achieved in an X-ray imaging system by providing collimation means in the form of shutters (12) to collimate the primary X-ray beam (1) such that the radiation (8) transmitted through a subject (4) to be imaged is incident substantially centrally on the active part (14) of an image detector (3), so as to define an active border (14*b*), in respect of which scatter levels can be measured. An electrical signal (104) representative of the scatter level is subtracted from the electrical signal (7) representative of the radiation (8) transmitted through the subject, to obtain a scatter-compensated image signal (106).

10 Claims, 5 Drawing Sheets

SCATTER COMPENSATION IN AN X-RAY SYSTEM

This invention relates generally to scatter compensation in an X-ray system and, more particularly, to a method and apparatus for real-time compensation for loss of contrast caused by scatter in monoplane and biplane X-ray systems.

X-ray imaging systems are commonly used for medical diagnostic purposes and for non-destructively inspecting the internal composition of various structures. Referring to FIG. 1 of the drawings, a typical monoplane X-ray imaging system comprises an X-ray source 2 and an image detector 3. The X-ray source 2 is fed by an X-ray generator comprising a high voltage generator 5 and a control unit 6. A patient or specimen 4, located between the X-ray source 2 and the image detector 3, is irradiated by an X-ray beam 1 and the elements of the specimen 4 attenuate the radiation. The image detector detects the attenuated radiation and an electrical signal representative of the intensity distribution of the radiation transmitted through the specimen 4 is generated. The electrical signal is then used to create an image of the exposed portion of the specimen 4 on a suitable monitor (not shown). Automatic Exposure Control (AEC) means (not shown) are generally provided to effect automatic control of the radiation dose to which the subject 4 is exposed.

Referring to FIG. 2 of the drawings, a typical biplane X-ray imaging system is arranged to obtain images of a subject 4 in two, often (approximately) perpendicular directions: namely, frontal (anterior-posterior or AP) view and side (lateral) view. Thus, the illustrated system comprises a frontal X-ray source 2a and a lateral X-ray source 2b, each generating a respective X-ray beam 1a, 1b, the axes of which beams are substantially perpendicular to each other. The subject 4 is irradiated by the X-ray beams 1a, 1b and respective image detectors 3a, 3b detect the intensity of radiation transmitted through the subject 4 and generate respective electrical signals 7a, 7b representative thereof. An image is then constructed using both electrical signals 7a, 7b and displayed on a suitable monitor (not shown).

In all X-ray imaging systems, the total flux of detected radiation consists of not only photons that did not interact with the elements of the attenuating subject 4 being imaged, but also of radiation scatter. Thus, referring to FIGS. 1 and 3, X-rays 8 incident on the image detector 3 having passed through the subject 4 being imaged contain not only primary X-rays, but also X-rays which are scattered by the subject 4 under examination. Such scattering occurs, at least in principle, in all directions, and the scattered X-rays constitute one of the major causes of deteriorated contrast and resolution in the transmitted X-ray image. In the monoplane system illustrated in FIG. 1, primary scatter 10 is invoked as the X-ray beam 1 passes through the subject 4. In a biplane system, such as that described with reference to FIG. 2 and illustrated also in FIG. 3, primary scatter 10a (10b) is also invoked as the corresponding X-ray beam 1a passes through the subject 4. However, in addition, scattered X-rays in the beam 8a incident on the image detector 3a also include scatter ("backscatter") 10b originating from the opposite X-ray beam 1b, and scattered X-rays in the beam 8b incident on the image detector 3b also include backscatter 10a originating from the opposite X-ray beam 1a. This can cause additional problems, particularly if both the frontal and lateral planes are active at the same time, including contrast reduction caused by both primary scatter and backscatter.

The most common method of X-ray scatter reduction is the antiscatter grid, which is a device having a series of lead blades lined up in parallel, which blades preferentially absorb scattered radiation and primarily pass non-scattered radiation. Another known solution to the problems caused by scatter in a biplane system is to irradiate the subject alternately in each plane, thereby avoiding interaction between the two X-ray beams and reducing contrast loss accordingly. However, for detectors with a fixed integration window, either the effective frame speed or the maximum exposure time is reduced, thereby reducing the Signal to Noise Ratio.

In an alternative known solution, scatter can be compensated for using a software simulation based on scatter models. Along similar lines, U.S. Pat. No. 6,633,626 proposes the use of a scatter-correction algorithm to eliminate the need to use an antiscatter grid in X-ray mammographic imaging. A method is described for removing scatter in an image, comprising the steps of acquiring data of an object of interest and using an iterative equation, including a thickness-dependent kernel modulation factor, to reconstruct an image of the subject being imaged.

However, this type of scatter compensation can be relatively slow to effect, and is therefore generally not particularly suitable for real-time applications.

It is an object of the present invention to provide a method and system for use in an X-ray imaging system (and corresponding X-ray imaging method) for compensating for scatter in an X-ray imaging system, which is suitable for use in both monoplane and multiplane systems to effect scatter compensation in real time conditions.

According to the present invention, there is provided an X-ray imaging system comprising an X-ray source for generating a primary X-ray beam, an image detector for detecting, and generating an electrical signal representative of, radiation transmitted through a subject to be imaged located between said X-ray source and said image detector, and collimator means provided between said X-ray source and said subject to be imaged for collimating said primary X-ray beam, said image detector having a defined active area and said collimator means being arranged and configured to collimate said primary X-ray beam such that said radiation transmitted through said subject is incident on a portion of said active area of said image detector, and means for determining a scatter level from a signal generated in respect of a portion of said active area of said image detector outside of the area thereof on which said transmitted radiation is incident.

The present invention provides a mechanism whereby the adverse effects (including most significantly contrast reduction) caused by primary scatter in monoplane X-ray imaging systems, and by primary scatter and backscatter in biplane X-ray imaging systems, can be compensated for in real-time, with the added advantage that, in biplane systems, the planes can (at least partly) be activated at the same time, so as to enable a larger exposure time or higher framespeed to be used.

Thus, the X-ray imaging system may comprise a monoplane or a multiplane (e.g. biplane) X-ray imaging system. In one exemplary embodiment of the present invention, the collimating means may comprise one or more shutters, defining a selectively closeable opening through which the X-ray beam passes to irradiate the subject. Preferably, the opening defined by the one or more shutters has an area which is less than the active area of the image detector. In a preferred embodiment, the radiation transmitted through the subject is arranged to be incident substantially centrally on the active area of the image detector, thereby defining an active border at the edge of the active area of the image detector, which may or may not have a substantially uniform width, wherein scatter is measured or otherwise determined within said active border. Scatter level may be determined by obtaining one or more electrical signals generated by said image detector in respect of said active border, and either determining an average value or subjecting said signal to an iterative algorithm. In fact, the shape of the portion of the active area used to determine scatter distribution in the image will depend on the scatter distribution itself, the algorithm used to determine such scatter distribution in the image and on the required extent and accuracy of the compensation. As an example, a spherical object might cause a rather homogeneous scatter pattern, in which case it is possible to measure the scatter distribution for use as an input for the compensation algorithm. In fact an optimum solution could be determined for each application.

The X-ray imaging system beneficially comprises means for displaying an image of said subject, whereby the portion of the active area of the image detector used for determining said scatter level is masked from view by a user on said display means.

Also in accordance with the present invention, there is provided a system for compensating for scatter in an image obtained using an X-ray imaging system defined above, the image comprising a plurality if picture elements derived from radiation incident on the active area of the image detector, the system comprising means for receiving data representative of a scatter level determined by said scatter level determining means, and means for adjusting each of said picture elements in accordance with said scatter level.

Still further in accordance with the present invention, there is a method of compensating for scatter in an image obtained using an X-ray imaging system defined above, the image comprising a plurality of picture elements derived from radiation incident on the active area of the image detector, the method comprising receiving data representative of a scatter level determined by said scatter level determining means, and adjusting each of the picture elements in accordance with said scatter level.

In one exemplary embodiment of the invention, the scatter level measurement can be applied directly to the picture elements to effect scatter compensation. Thus, the system may comprise means for generating an electrical signal representative of the scatter level, and means for subtracting the electrical signal from said electrical signal representative of the radiation transmitted through the subject.

Alternatively, or in addition, the scatter level measurement(s) effected by the scatter level determining means may be employed to generate and/or refine scatter compensation values for use in 3D image processing algorithms, which 3D image processing algorithms have the added benefit of reducing artefacts (i.e. less cupping, fewer streaks) in the resultant three-dimensional image reconstruction. Thus, in a first exemplary embodiment, means may be provided for obtaining a single scatter level in respect of said image, and adjusting at least some (and preferably each) of said picture elements to compensate for said single scatter level. Alternatively, means may be provided for generating a scatter profile defining a pattern of estimated scatter levels in respect of each of said picture elements of said image, and adjusting said scatter profile in accordance with one or more scatter levels determined by said scatter level determining means. As will be apparent to a person skilled in the art, such a scatter profile may, for example, be generated using data representative of a radiation dose applied to the subject by the X-ray source and an algorithmic scatter model.

These and other aspects of the present invention will be apparent from, and elucidated with reference to, the embodiment described herein.

An embodiment of the present invention will now be described by way of example only and with reference to the accompanying drawings, in which.

Figure 1:
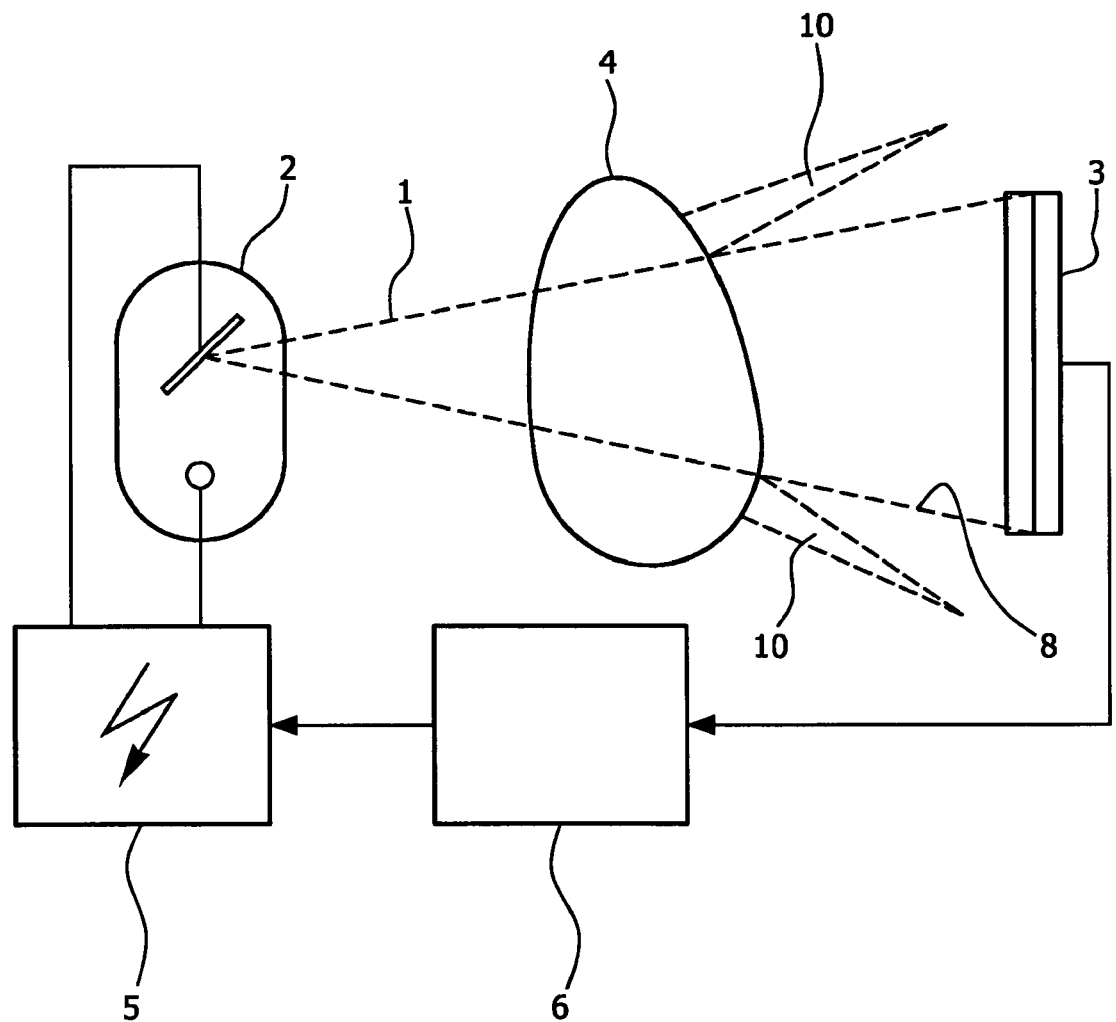
FIG. 1 is a schematic diagram illustrating the principle components of a monoplane X-ray imaging system.
Figure 2:
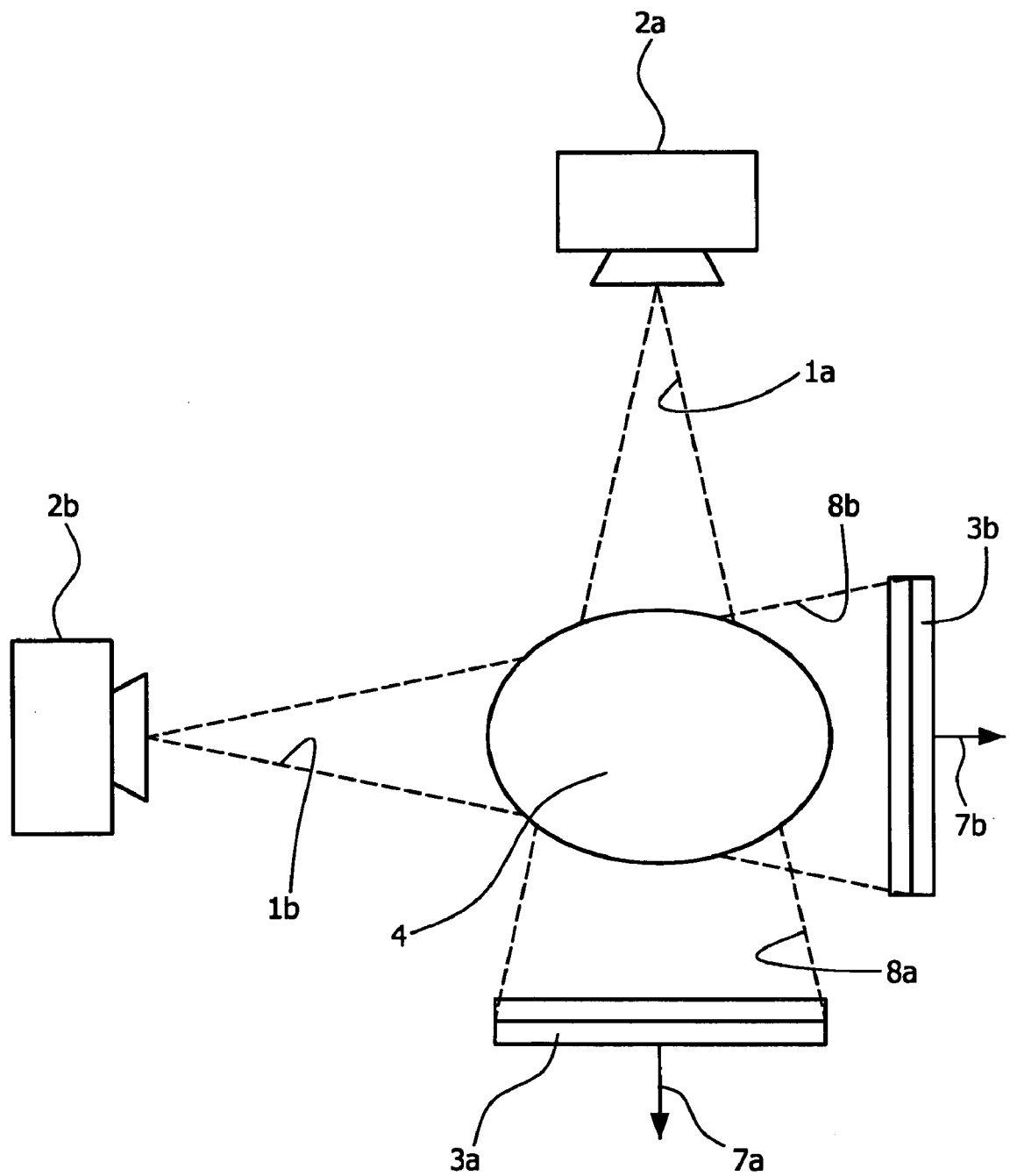
FIG. 2 is a schematic diagram illustrating the principle components of a biplane X-ray imaging system.
Figure 3:
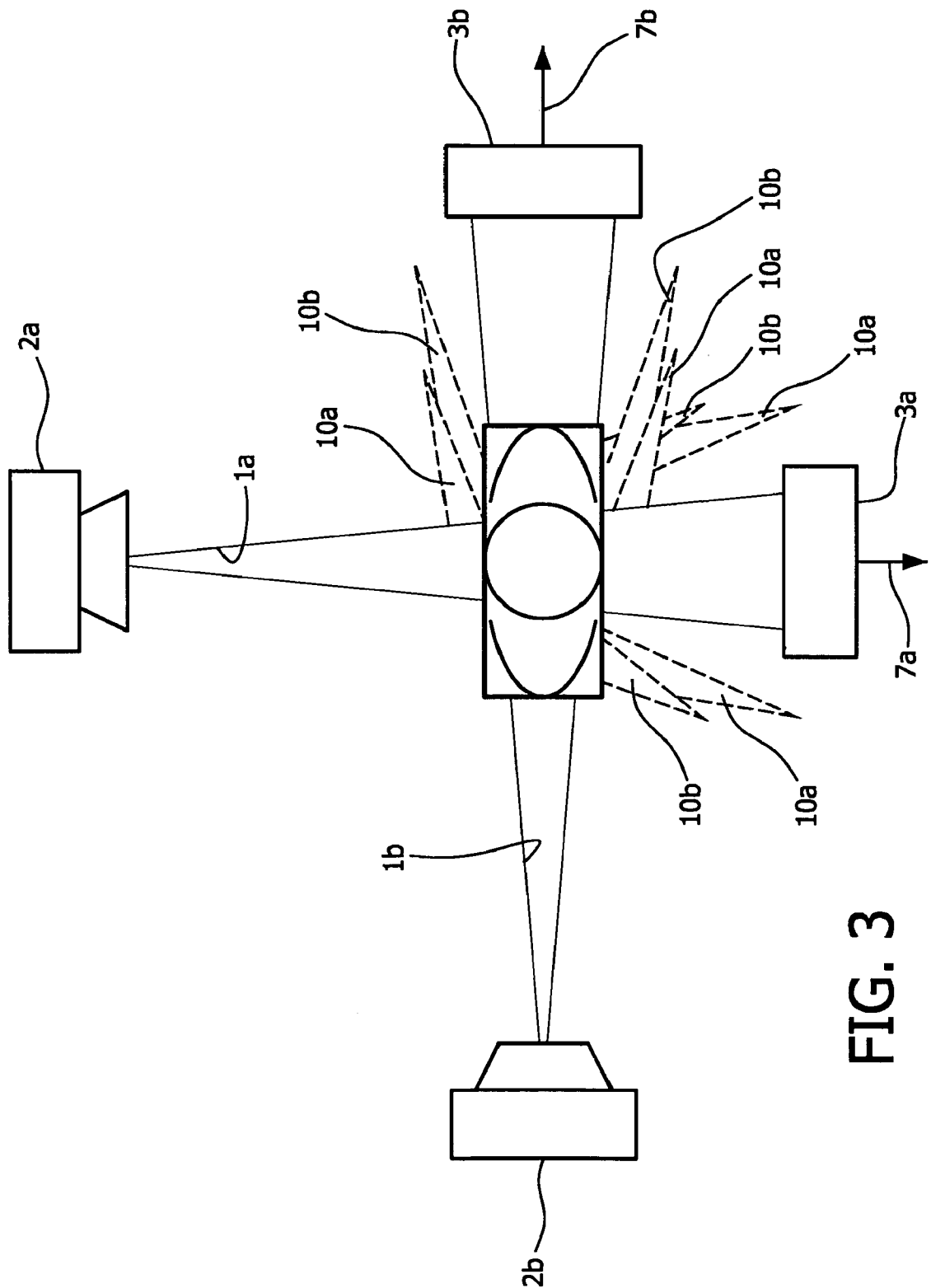
FIG. 3 is a schematic diagram of the biplane system of FIG. 2, illustrating the components of scatter occurring therein.
Figure 4:
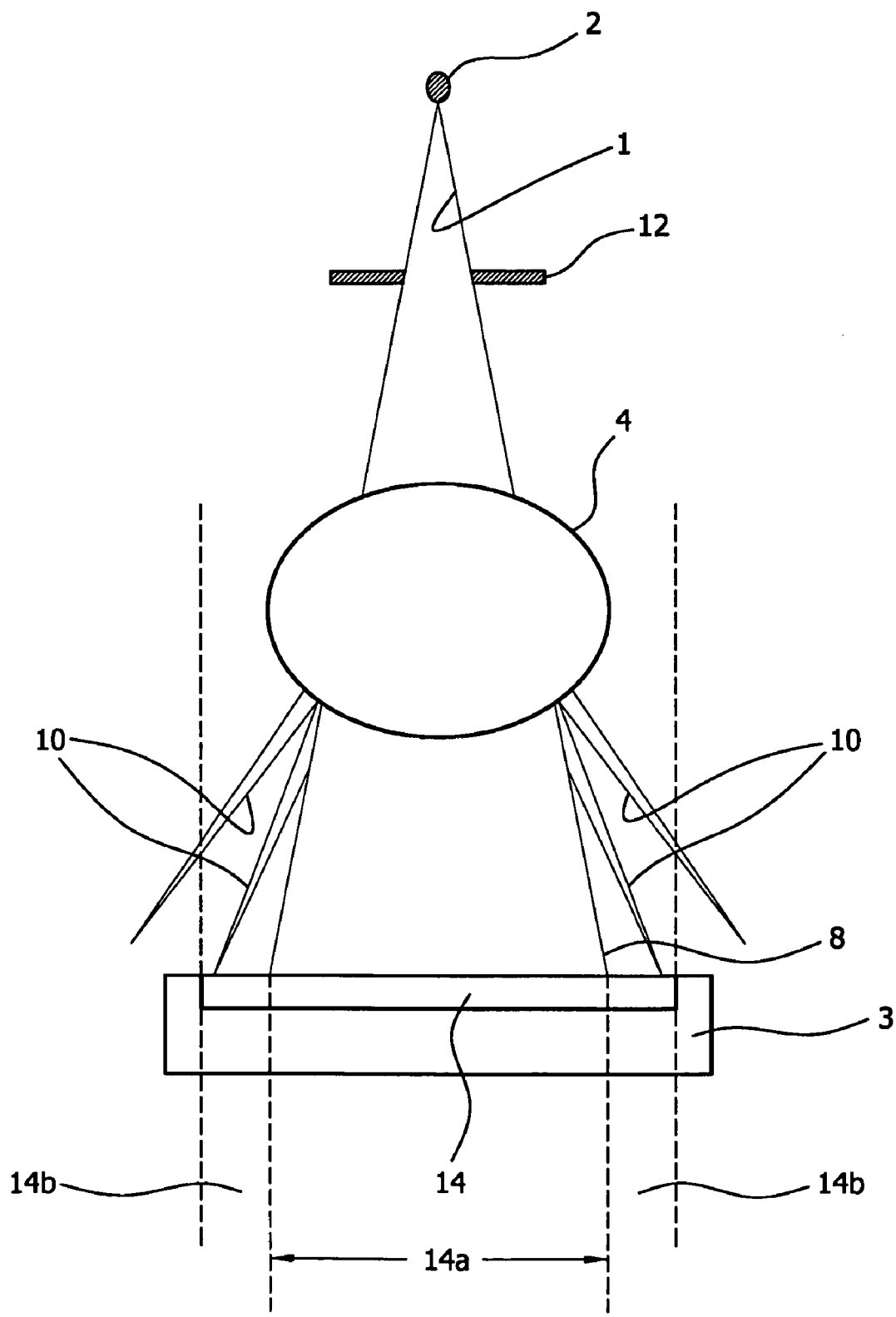
FIG. 4 is a front schematic view of the principle components of an X-ray imaging system according to an exemplary embodiment of the present invention.
Figure 5:
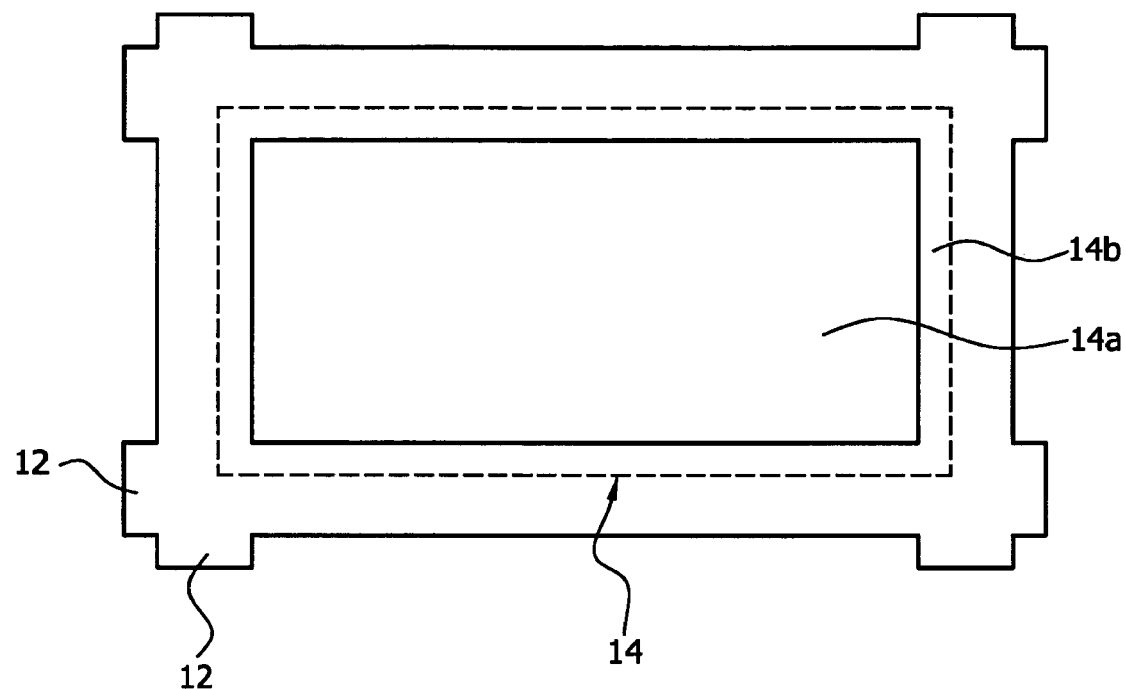
FIG. 5 is a schematic plan view of the components illustrated in FIG. 4.

Referring to FIGS. 4 and 5 of the drawings, an X-ray imaging system according to an exemplary embodiment of the present invention comprises an X-ray source 2 for generating an X-ray beam 1, whereby a flat image detector 3 is provided for detecting radiation 8 transmitted through a subject 4 to be imaged, as described with reference to the prior art.

Shutters 12, which form part of a collimator arrangement, are provided between the X-ray source 2 and the subject 4 to be imaged, for collimating the X-ray beam 1. The image detector 3 has an active area 14 for receiving radiation and generating electrical signals representative of the image intensity thereof. The collimator arrangement, including the shutters 12, is arranged and configured to generate an irradiating X-ray beam having an area slightly less than that of the active area 14 of the image detector 3. Thus, image intensity of the attenuated X-ray beam 8 is measured in a substantially central portion 14a of the active area 14 of the image detector 3. The remaining border 14b of the active area 14 of the image detector is used to measure scatter levels in relation to scattered radiation 10 incident thereon. Purely as an example, it is envisaged that a suitable radiation measuring area 14a for a cardiac X-ray imaging application might be around 2 cm$^2$ with a scatter-measuring border 14b of, say, 1 pixel. It will be appreciated by a person skilled in the art that, when the X-ray system is angulated relative to a subject, the position of the measuring border 14b relative to the active area 14 of the image detector may change accordingly, and compensation techniques (e.g. mechanical or electronic read out compensation techniques) for dealing with this issue are known.

Figure 6:
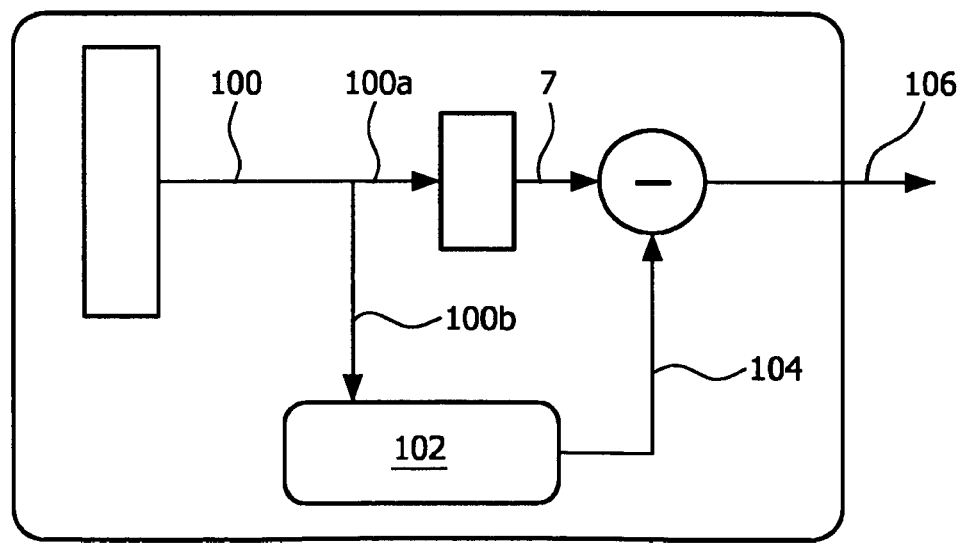
FIG. 6 is a schematic flow diagram illustrating the scatter compensation principal employed in an X-ray imaging system according to an exemplary embodiment of the present invention.

This scatter level may, for example, be calculated on the basis of an average value, or using an iterative algorithm. However, other suitable methods will be apparent to a person skilled in the art. In any event, and referring additionally to FIG. 6 of the drawings, an image matrix 100 representative of radiation detected in the active area 14 of the image detector 3 is received, and split into two components: a main component 100a derived from the radiation detected in the central portion 14a of the active area 14 of the image detector 3, and a scatter component 100b derived from the scatter detected in the border 14b of the image detector 3. The main component 100a is processed to generate an electrical image signal 7, as in the prior art. The scatter component is processed (at 102) to measure a scatter level (using any suitable method, as mentioned above), and an electrical signal 104 representative thereof is generated accordingly. The scatter signal 104 is subtracted from the image signal 7 to generate a scatter-compensated image signal 106, which is used to create a displayed image, in which the scatter measuring border 14b of the active area 14 of the image detector 3 is preferably masked from view by the user (using image processing techniques) in the final displayed image. A suitable method of measuring scatter (intensity) level in the measuring border 14b is to calculate the average value of this information and to subtract this (at least partially) from the video image. More complex possibilities include determining the "scatter image" (spatial scatter contribution) and subtracting it from the image. This can be done with or without additional information from the system.

Three-dimensional (3D) reconstruction of an object from a rotational scan has as its aim, to determine the attenuation of each of its 3D voxels from the two-dimensional projections derived from radiation detected in the active area 14 of the image detector 3. This type of three-dimensional image reconstruction is also affected by the scatter present in the projections: scatter adds a DC (or low frequency) component to the projections and, since attenuation is normally determined from taking the logarithm of the projections, a nonlinear scatter component destroys the attenuation measurement [i.e. log(primary+scatter radiation) instead of log(primary radiation)], giving rise to an underestimation of patient attenuation, particularly in the centre of the patient, although less severely at the boundaries (since primary radiation>>scatter at the boundaries). In particular, soft tissue imaging (which is very much like CT imaging) suffers from inaccuracies caused by scatter present in the two-dimensional projections, since it aims to show minute differences in attenuation occurring between, for instance, fat and muscle or ventricles and brain matter. The above-mentioned underestimation in attenuation makes it very difficult to select a greylevel window for viewing the reconstruction that will allow small attenuation differences over an entire slice to be visualised. This effect (i.e. lower grey levels in the middle than at the edges) is called "cupping". In addition, scatter adds noise to the projection, which results in noise in the reconstruction and also makes it more difficult for differences in attenuation to be seen in the resultant 3D reconstruction.

The scatter measurement techniques proposed above can be used to correct the two-dimensional projection derived from the radiation detected in the central portion 14a of the active area 14 of the image detector 3, for the scatter component so as to effect more accurate 3D image reconstruction. However, although the scatter measurement and direct application of the measured value(s) in scatter compensation reduce the "cupping" effect described above, noise is not significantly reduced. At least as important as noise reduction in the field of 3D image reconstruction is the reduction of artefacts (i.e. to achieve fewer streaks and less cupping in the 3D image), and more complex possibilities for dealing with this issue therefore include the use of image-based scatter algorithms in 3D image processing techniques. The simplest approach may, for example, comprise taking a single scatter intensity value (measured at the border 14b of the active area 14 of the image detector 3) and applying an image processing technique to correct all pixels in the two-dimensional projection for scatter. This is quite an accurate technique, since the scatter is only dominant in the dark pixels of the projection. The scatter contribution to pixels hit by direct radiation is relatively very small. More complex possibilities include determining a "scatter image" or scatter profile (representative of spatial scatter contribution over the pixels of the entire image) and using the scatter intensity detected at the border 14b of the image detector to refine this scatter profile. For example, a two-dimensional projection in combination with a known entrance (radiation) dose and a (known) scatter model can be used to estimate scatter, which scatter model can be refined by the measured values obtained from the edges (i.e. the border 14b) of the image.

In one exemplary embodiment of the invention, it may be desirable to subtract the entire scatter level signal 104 from the image signal 7 to obtain the scatter-compensated image signal 106. On the other hand, it may be preferable to only partially compensate for scatter. The choice between full or partial scatter compensation is likely to depend upon the same factors as the shape of the portion of the active area used to measure scatter distribution, including image content and the scatter measuring algorithm employed, as will be apparent to a person skilled in the art. Consideration for full or partial scatter compensation will mainly be based on the achievable accuracy of the compensation. In other words, if the accuracy of the scatter compensation is limited, partial compensation would prevent artefacts in the images.

The present invention offers significant advantages in scatter compensation relative to the prior art. Particularly in relation to biplane X-ray imaging systems, where only very short X-ray exposure windows are available, simultaneous radiation (in both planes) is made possible by the mechanism of the present invention (because scatter from the opposite plane can also be compensated for), thereby enabling larger exposure times to be provided with less noise and a lower kV supply requirement. However, the present invention provides equally valuable advantages in relation to monoplane imaging systems, particularly in the case of paediatric applications where relatively small features are required to be imaged with a relatively high resolution and contrast. In both cases, no additional information is required to effect scatter compensation, and the present invention provides the ability to effect real-time scatter compensation, which makes it equally suitable for applications where image contents change during a run e.g. during processes such as fluoroscopy and the like.

The proposed method of scatter compensation also works to exclude scatter from Automatic Thickness Correction (ATC), which is the part of the system that determines patient thickness during radiation (e.g. during fluoroscopy) by measuring the patient input dose level (determined by X-ray tube voltage and current, and exposure time), measuring patient output dose level (determined by the detector dose level), calculating the patient thickness (in water equivalents) using the actual X-ray tube voltage as a parameter, and then calculating optimum start parameters (tube voltage, tube current, etc) for the next radiation sequence (run or single shot), taking into account a certain detector dose level, X-ray tube capabilities, etc. Equally, the proposed method of scatter compensation can be used in combination memory effect correction applications, wherein memory effects in a flat X-ray detector particularly visible in fluoroscopy when a fluoroscopy run has been preceded by a high dose exposure run, are compensated for.

Systems are known in which scatter correction is effected by estimating the shape of the scatter distribution in respect of an X-ray image, i.e. no absolute value or scatter level measurement is obtained. For example, European Patent No. 0358268 describes a system in which an image matrix is generated from a digital image signal derived from an analog X-ray detector image signal, the image matrix is then transformed by convolution with a point spread function and weighting factors are applied depending on local intensity values, and the transformed image matrix (which is representative of the estimated scatter distribution) is subtracted from the image matrix. The present invention could be used to further refine or supplement this type of technique by additionally enabling scatter compensation to be effected directly using scatter level measurements obtained from the measuring border 14b and/or by enabling the weighting factors and/or the point spread function to be more accurately derived using the absolute values obtainable by means of the present invention.

It should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The word "comprising" and "comprises", and the like, does not exclude the presence of elements or steps other than those listed in any claim or the specification as a whole. The singular reference of an element does not exclude the plural reference of such elements and vice-versa. The invention may be implemented by means of hardware comprising several distinct elements, and by means of a suitably programmed computer. In a device claim enumerating several means, several of these means may be embodied by one and the same item of hardware. The mere fact that certain measures are recited in mutually different dependent claims does not indicate that a combination of these measures cannot be used to advantage.

The invention claimed is:

1. An X-ray imaging system comprising
   a) an X-ray source for generating a primary X-ray beam,
   b) an image detector for detecting, and generating an electrical signal representative of, radiation transmitted through a subject to be imaged located between said X-ray source and said image detector
   c) collimator means provided between said X-ray source and said subject to be imaged for collimating said primary X-ray beam, said image detector having a defined active area and said collimator means being arranged and configured to collimate said primary X-ray beam such that said radiation transmitted through said subject is incident on a portion of said active area of said image detector, and
   d) means for determining a scatter level from a signal generated in respect of a portion of said active area of said image detector outside of the area thereof on which said transmitted radiation is incident, wherein the portion of the active area for which the scatter level is determined borders the entire area on which the transmitted radiation is incident.

2. The system according to claim 1, wherein said collimating means comprise one or more shutters, defining a selectively closeable opening through which the X-ray beam passes to irradiate the subject.

3. The system according to claim 2, wherein said opening defined by said one or more shutters has an area which is less than the active area of the image detector.

4. The system according to claim 1, further comprising means for displaying an image of said subject, whereby the portion of the active area of the image detector used for determining said scatter level is masked from view by a user on said display means.

5. A system for compensating for scatter in an image obtained using an X-ray imaging system according to claim 1, said image comprising a plurality of picture elements derived from radiation incident on said active area of said image detector, the system further comprising means for receiving data representative of a scatter level determined by said scatter level determining means, and means for adjusting each of said picture elements in accordance with said scatter level.

6. The system according to claim 5, further comprising means for generating an electrical signal representative of said scatter level, and means for subtracting said electrical signal representative of said scatter level from said electrical signal representative of said radiation transmitted through said subject.

7. The system according to claim 5, further comprising means for obtaining a single scatter level in respect of said image, and adjusting at least some of said picture elements to compensate for said scatter level.

8. The system according to claim 5, further comprising means for generating a scatter profile defining a pattern of estimated scatter levels in respect of each of said picture elements of said image, and adjusting said scatter profile in accordance with one or more scatter levels determined by said scatter level determining means.

9. The system according to claim 8, wherein said scatter profile is generated using data representative of a radiation dose applied to said subject by said X-ray source and an algorithmic scatter model.

10. A method for compensating for scatter in an image obtained using an X-ray imaging system according to claim 1, said image comprising a plurality of picture elements derived from radiation incident on said active area of said image detector, the method comprising receiving data representative of a scatter level determined by said scatter level determining means, and adjusting each of said picture elements in accordance with said scatter level.

* * * * *